(12) United States Patent
Dorff et al.

(10) Patent No.: US 12,396,854 B2
(45) Date of Patent: Aug. 26, 2025

(54) SYSTEMS, DEVICES AND METHODS FOR RESHAPING A BODILY LUMEN

(71) Applicant: Medtronic, Inc., Minneapolis, MN (US)

(72) Inventors: Caitlin M. Dorff, Santa Rosa, CA (US); William A. Berthiaume, Santa Rosa, CA (US); Emily A. Grimm, Petaluma, CA (US); Matthew E. Genovese, Windsor, CA (US); Michael A. Gloss, Minneapolis, MN (US); William W. Chang, Santa Rosa, CA (US); Karan P. Punga, San Rafael, CA (US); Fatemeh Fatemi Far, Santa Rosa, CA (US)

(73) Assignee: Medtronic, Inc., Santa Rosa, CA (US)

( * ) Notice: Subject to any disclaimer, the term of this patent is extended or adjusted under 35 U.S.C. 154(b) by 516 days.

(21) Appl. No.: 17/714,732

(22) Filed: Apr. 6, 2022

(65) Prior Publication Data
US 2022/0362022 A1  Nov. 17, 2022

Related U.S. Application Data

(60) Provisional application No. 63/187,603, filed on May 12, 2021.

(51) Int. Cl.
*A61F 2/24* (2006.01)
*A61F 2/00* (2006.01)

(52) U.S. Cl.
CPC .......... *A61F 2/2466* (2013.01); *A61F 2/0036* (2013.01); *A61F 2220/0016* (2013.01); *A61F 2220/0075* (2013.01)

(58) Field of Classification Search
CPC ............ A61F 2/2466; A61F 2220/0016; A61F 2220/0075; A61F 2/2445;
(Continued)

(56) References Cited

U.S. PATENT DOCUMENTS

| 5,423,857 A | 6/1995 | Rosenman |
| 8,968,393 B2 | 3/2015 | Rothstein |

(Continued)

FOREIGN PATENT DOCUMENTS

| EP | 2723274 B1 | 4/2014 |
| WO | 2005/046488 A2 | 5/2005 |
| WO | 2010/030842 A2 | 3/2010 |

OTHER PUBLICATIONS

Extended European Search Report, EP Application No. 22171598.0, date Oct. 6, 2022, 8 pages.
(Continued)

*Primary Examiner* — Jerrah Edwards
*Assistant Examiner* — Hanna L Pasqualini
(74) *Attorney, Agent, or Firm* — Medler Ferro Woodhouse & Mills PLLC

(57) ABSTRACT

Aspects of the disclosure include bodily lumen reshaping and reduction systems, devices and methods. Such implants can include a plurality of anchors serially interconnected with a cinching member. Delivery devices of the disclosure are configured to deploy a first anchor into tissue. The delivery device can then deploy a second anchor and wind the cinching member around the second anchor to reduce a distance between the first and second anchors, placating the tissue between the anchors. Additional anchors can be similarly deployed and the cinching member can be similarly adjusted to reshape the lumen. Methods of deploying and reshaping a bodily lumen are also disclosed. In various examples, the bodily lumen is a heart valve, atrial appendage, portion of a gastrointestinal tract or urethra. Various embodiments include one or more anchors having a ratchet assembly or the like to substantially prevent the cinching member from unwinding.

20 Claims, 14 Drawing Sheets

(58) Field of Classification Search
CPC .. A61F 2220/0008; A61F 2/2442; A61F 2/24; A61F 2220/00; A61M 25/00; A61B 17/00; A61B 17/064
See application file for complete search history.

(56) References Cited

U.S. PATENT DOCUMENTS

| | | |
|---|---|---|
| 2004/0093024 A1 | 5/2004 | Lousararian |
| 2004/0236419 A1 | 11/2004 | Milo |
| 2008/0027483 A1* | 1/2008 | Cartledge .......... A61B 17/0644 606/100 |
| 2010/0280605 A1* | 11/2010 | Hammer .............. A61B 17/068 623/2.11 |
| 2019/0336288 A1* | 11/2019 | Gross .................... A61F 2/2445 |
| 2019/0343626 A1 | 11/2019 | Smirnov et al. |
| 2020/0188108 A1* | 6/2020 | Grimm ................ A61F 2/2445 |
| 2021/0113212 A1 | 4/2021 | Lashinski et al. |

OTHER PUBLICATIONS

International Search Report and Written Opinion, International Application No. PCT/IB2022/055724, dated Oct. 5, 2022, 15 pages.

* cited by examiner

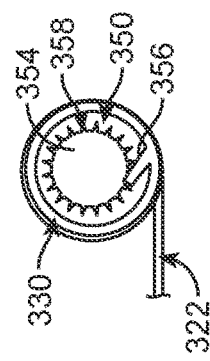
FIG. 13A
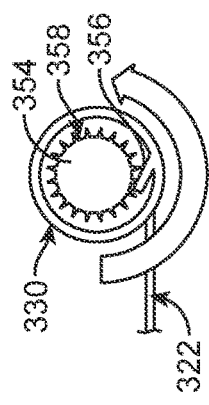
FIG. 13B
FIG. 13C
FIG. 13D
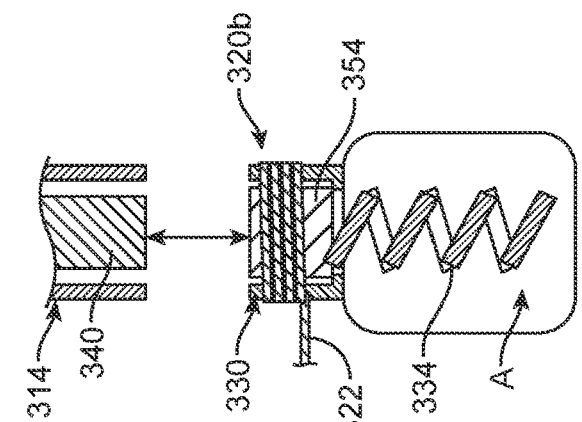
FIG. 14A
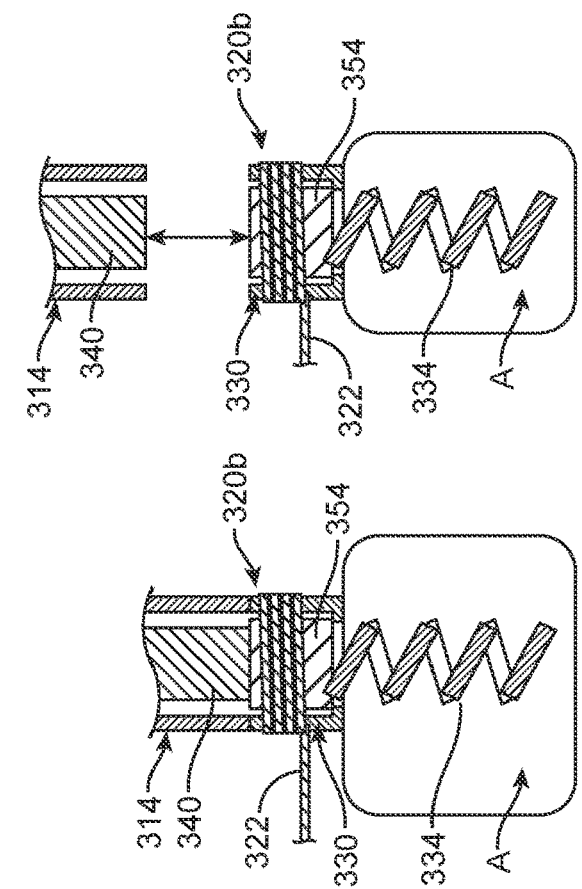
FIG. 14B
FIG. 14C
FIG. 14D

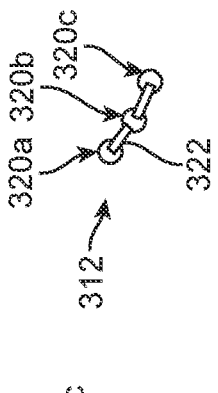
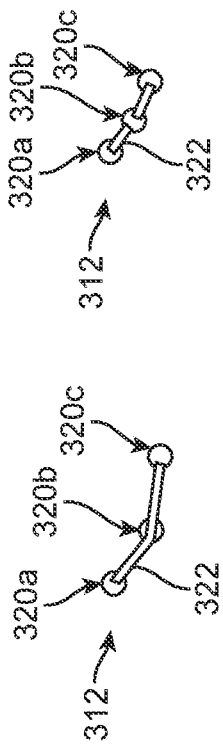
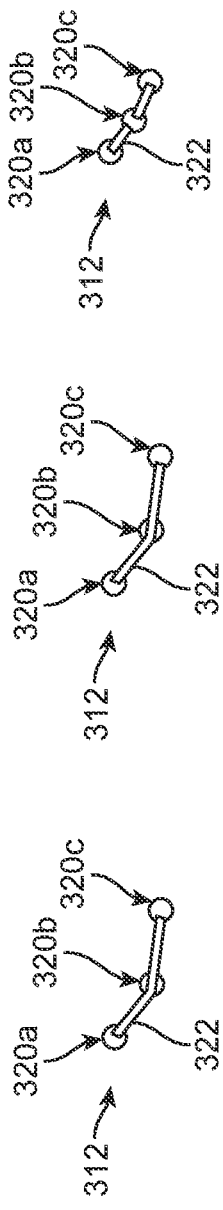
FIG. 15A  FIG. 15B  FIG. 15C
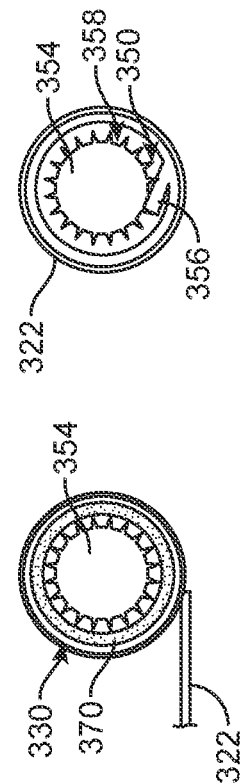
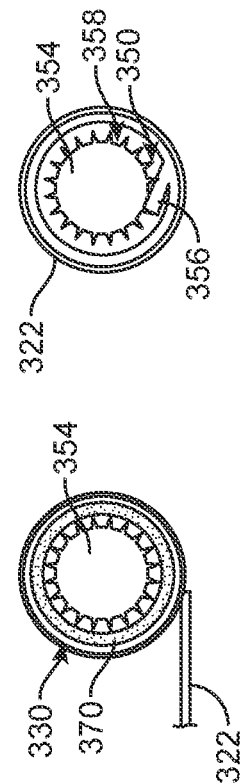
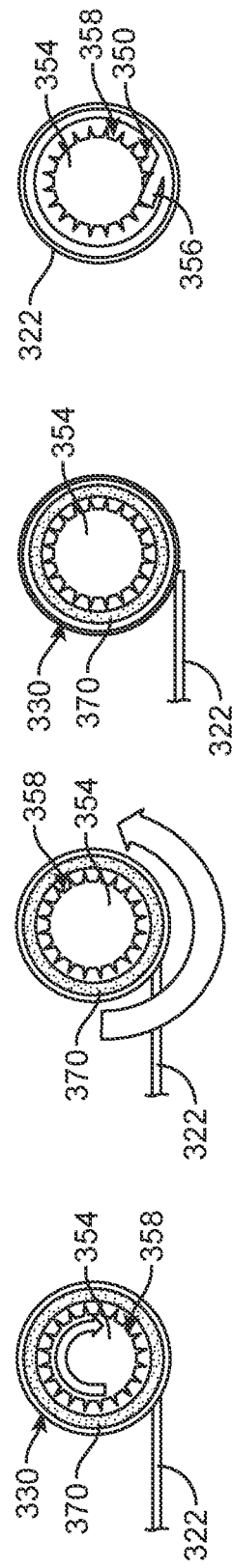
FIG. 16A  FIG. 16B  FIG. 16C  FIG. 16D

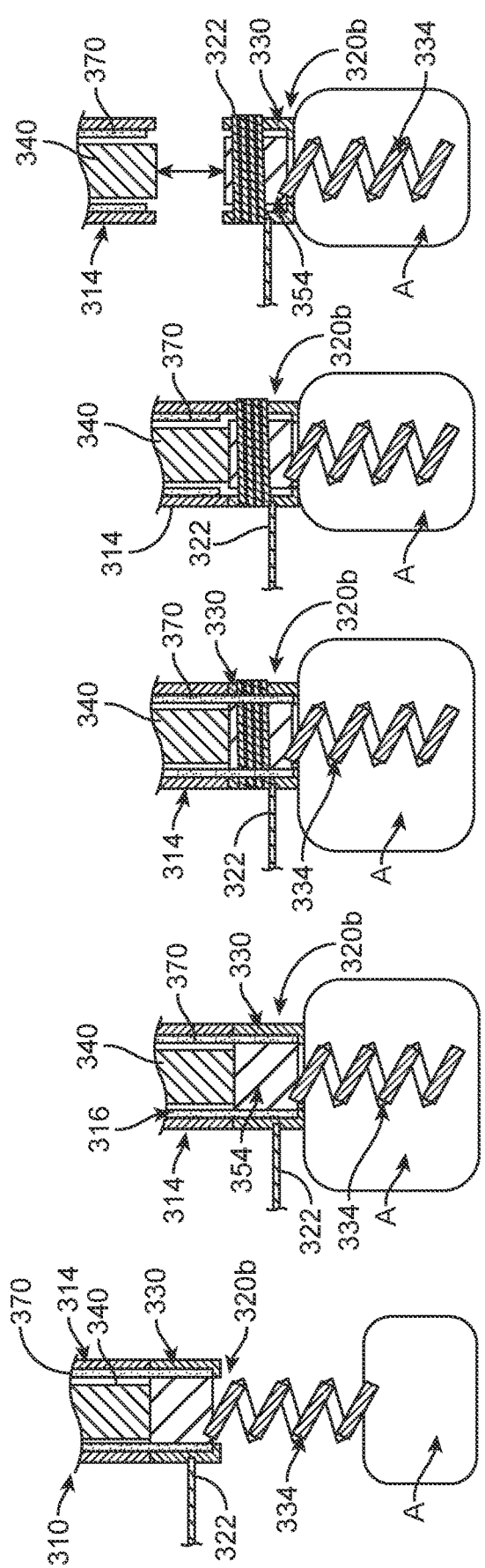

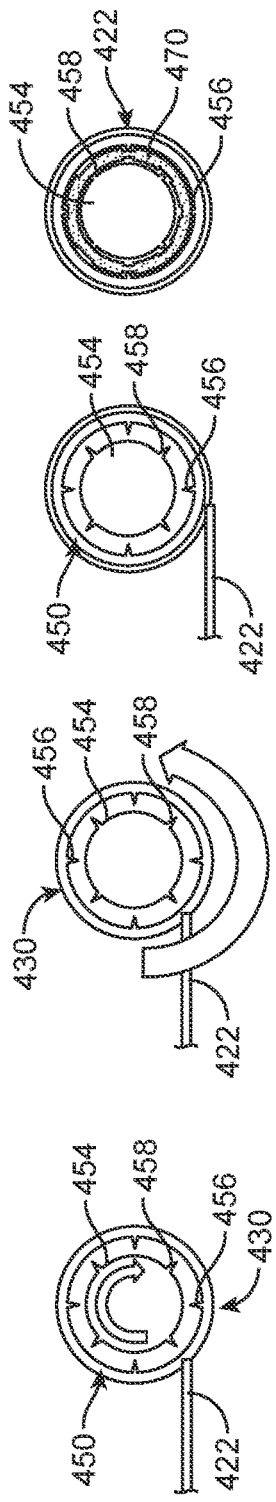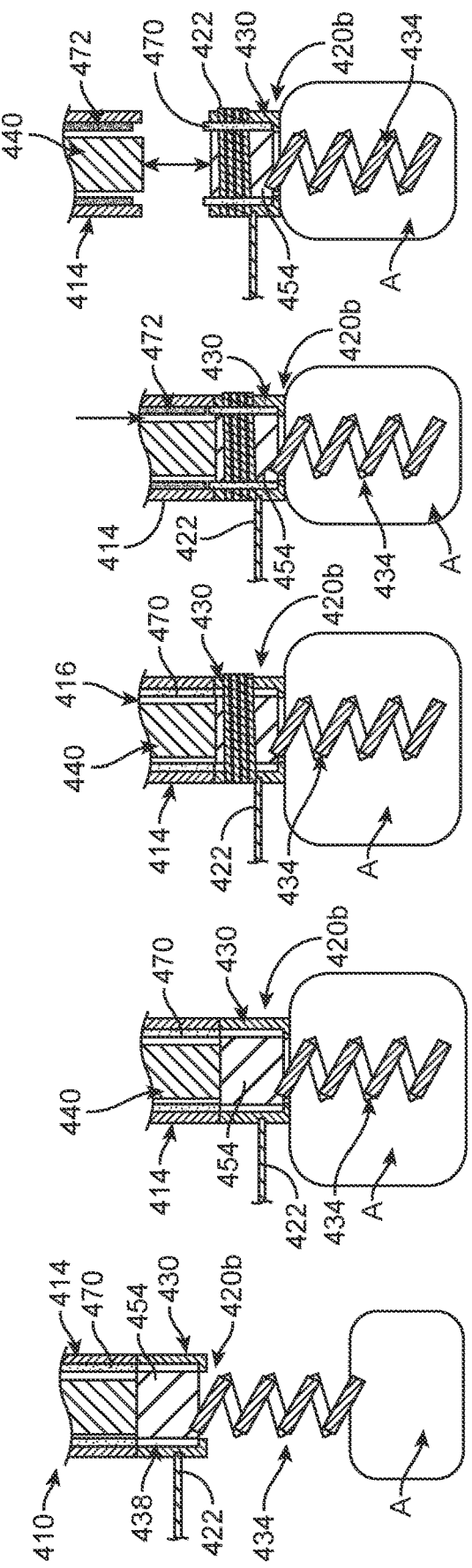

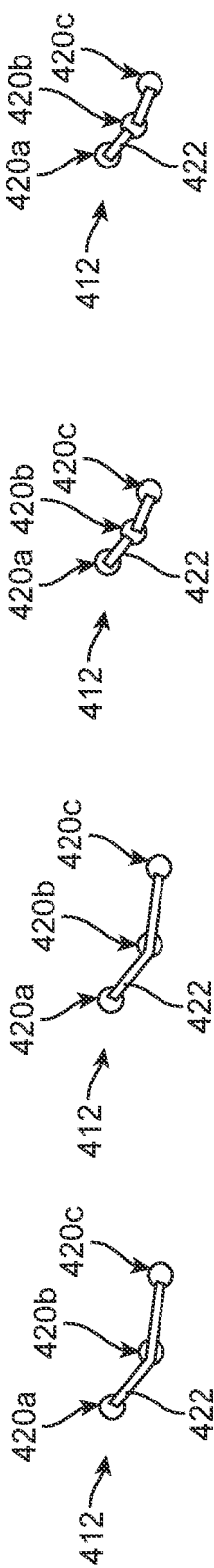

SYSTEMS, DEVICES AND METHODS FOR RESHAPING A BODILY LUMEN

CROSS-REFERENCE TO RELATED APPLICATIONS

This Non-Provisional patent application claims the benefit of the filing date of U.S. Provisional Patent Application Ser. No. 63/187,603, filed May 12, 2021, entitled "SYSTEMS, DEVICES AND METHODS FOR RESHAPING A BODILY LUMEN," the entire teachings of which are incorporated herein by reference.

FIELD

The present technology is generally related systems, devices and methods for reshaping a bodily lumen. In some examples of the disclosure, the bodily lumen is a heart valve annulus.

BACKGROUND

Generally, the anatomy and physiology of the human heart is well known. Of the four one-way valves in the heart, the two inlet valves are the mitral valve of the left side of the heart, and the tricuspid valve on the right side of the heart. The tricuspid valve is located between the right atrium and the right ventricle. The three leaflets of the tricuspid valve laterally terminate at the tricuspid annulus. Blood flows from the superior and inferior vena cava into the right atrium, then through the tricuspid valve during diastole to fill the right ventricle. During ventricular systole, the tricuspid valve is closed and blood is ejected through the pulmonary valve into the pulmonary artery and hence through the lungs. At the end of ventricular systole the pulmonary valve closes. Leaving the lungs, the now oxygenated blood flows into the left atrium and hence through the mitral valve into the left ventricle during ventricular diastole. Finally, at ventricular systole the mitral valve closes and blood is ejected through the aortic valve into the aorta. However, should the mitral valve become regurgitant due to disease then some percentage of the left ventricular stroke volume will flow backwards through the mitral valve into the left atrium. This regurgitation causes the left atrial pressure to rise, in turn causing pulmonary artery pressure to rise, which is reflected back to the right ventricular pressure.

Typically, to treat a patient with functional mitral regurgitation, a physician places an annuloplasty ring on the mitral annulus to reduce the circumference and septal-lateral diameter of the annulus. In degenerative mitral regurgitation patients, annuloplasty rings are utilize to stabilize the mitral annulus, not reduce the annular circumference.

The present disclosure addresses problems and limitations associated with the related art.

SUMMARY

The techniques of this disclosure generally relate to systems and methods of delivering an implant to a heart valve annulus for resizing of the valve annulus to treat regurgitation. Various examples of the disclosure provide for versatility and control in how multiple segments of the implant are reduced in length to allow patient-specific treatment and optional symmetry in resizing of the valve annulus. In addition, embodiments of the disclosure provide a relatively small delivery system, optionally under 25 French, allowing for increased safety in transcatheter and/or trans-septal delivery of the implant. It is further envisioned that aspects of the disclosure are suitable for reshaping or resizing other bodily lumens such as an atrial appendage, gastrointestinal tract or urethra, for example.

In one aspect, the present disclosure provides an implant including a first anchor and a second anchor, each of the first and second anchors having a head connected to a prong assembly. The implant further includes a cinching member interconnecting the first and second anchors. The cinching member is fixedly connected to the first anchor and is configured to wrap around the second anchor at least one revolution.

In another aspect, the present disclosure provides a system including a catheter defining a first lumen and an implant positioned within the first lumen. The implant has a plurality of anchors connected in series by a cinching member. At least one anchor has a head and a ratchet assembly positioned within the head. The ratchet assembly is configured to restrict movement of the cinching member in one direction.

In another aspect, the present disclosure provides methods of delivering an implant. Such methods can include providing a delivery device including a catheter defining a lumen. The delivery device is provided in a loaded arrangement in which an implant is positioned with the lumen. The implant has a plurality of anchors connected in series by a cinching member. The plurality of anchors include a first anchor and a second anchor. The method further includes delivering a distal end of the catheter to a first target site and deploying the first anchor into the first target site, moving the distal end of the catheter to a second target site and partially deploying the second anchor into the second target site, and rotating the second anchor to wrap the cinching member around the second anchor to shorten a first distance between the first and second anchors.

The details of one or more aspects of the disclosure are set forth in the accompanying drawings and the description below. Other features, objects, and advantages of the techniques described in this disclosure will be apparent from the description and drawings, and from the claims.

BRIEF DESCRIPTION OF DRAWINGS

FIG. 13A is a schematic illustration of an anchor suitable for use with implants of the disclosure, the implant including an alternate ratchet assembly.

FIGS. 13B-13D are schematic top views of the ratchet assembly of FIG. 13A as a cinching member of the implant is wound around the anchor.

FIGS. 14A-14D are schematic illustrations of implantation of the anchor of FIG. 13A, wherein FIGS. 14A-14C correspond with FIGS. 13B-13D.

FIGS. 15A-15C schematically illustrate a shortening of a distance between adjacent anchors of an implant to resize tissue secured to the implant using the method of FIGS. 14A-14C.

FIGS. 16A-16D illustrate an optional modification to the method of FIGS. 13A-14D in which a sleeve is positioned between ratchet teeth and a cam of the ratchet assembly to prevent engagement of the cam with the ratchet teeth until desired.

FIGS. 17A-17E are schematic illustrations of implantation of the anchor of FIG. 13A, wherein FIGS. 17A-17D correspond with FIGS. 16B-16D.

FIGS. 18A-18D schematically illustrate a shortening of a distance between adjacent anchors of an implant to resize tissue secured to the implant using the method of FIGS. 17A-17E.

FIGS. 19A-19D illustrate an alternate method utilizing a locking ring.

FIGS. 20A-20E are schematic illustrations of implantation of an, wherein FIGS. 20A-20D correspond with FIGS. 19B-19D.

FIGS. 21A-21D schematically illustrate a shortening of a distance between adjacent anchors of an implant to resize tissue secured to the implant using the method of FIGS. 20A-20D.

DETAILED DESCRIPTION

Specific embodiments of the present disclosure are now described with reference to the figures, wherein like reference numbers indicate identical or functionally similar elements. The terms "distal" and "proximal" are used in the following description with respect to a position or direction relative to the treating clinician. "Distal" or "distally" are a position distant from or in a direction away from the clinician. "Proximal" and "proximally" are a position near or in a direction toward the clinician.

Figure 1:
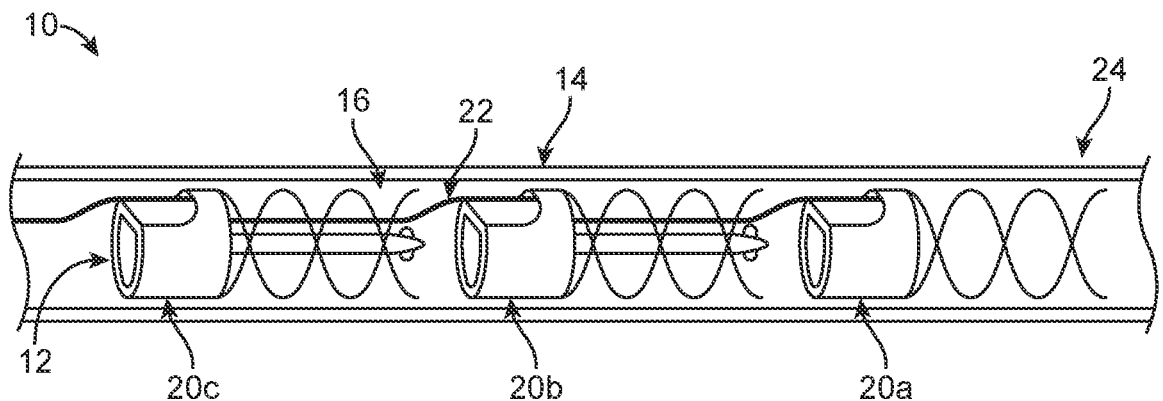
FIG. 1 is a partial, schematic illustration of a system of the disclosure including a catheter in which an implant having a plurality of anchors is positioned for delivery.
Figure 2:
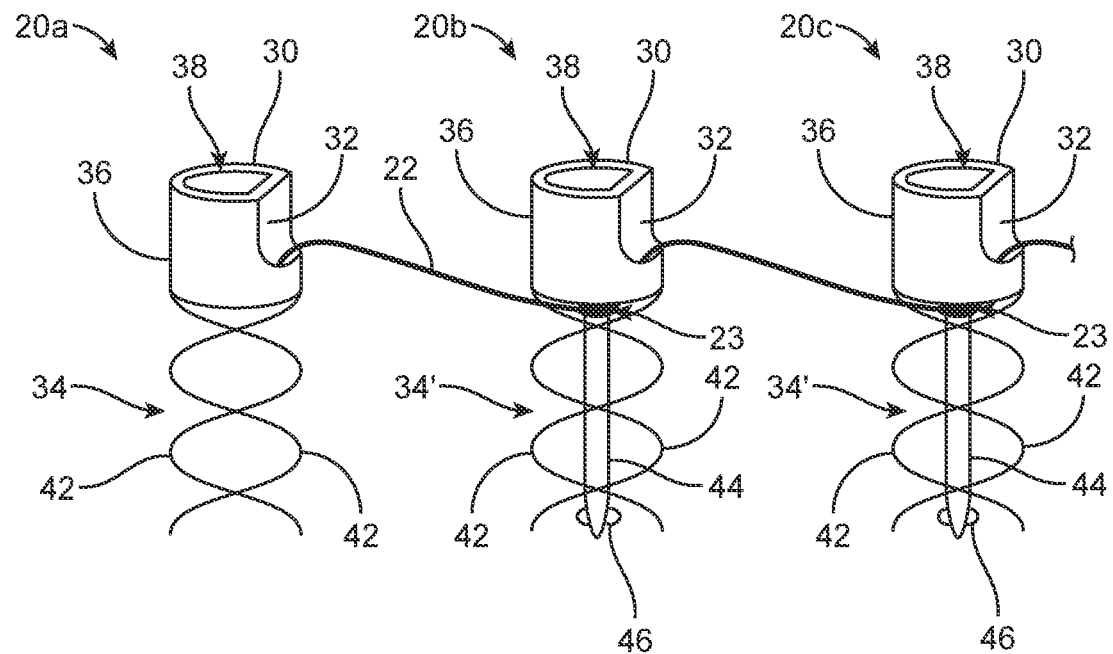
FIG. 2 is a partial, schematic illustration of the implant of FIG. 1.

Referring in particular to FIGS. 1-2, systems of the disclosure include a delivery device 10 for delivering an implant 12 to a bodily lumen to be resized. In many examples of the disclosure, the bodily lumen or tissue described is a heart valve annulus, such as a mitral or tricuspid valve annulus. Such examples are provided merely as illustrative examples and aspects of the present disclosure are not intended to be limited to any particular bodily lumen. In one example, the delivery device 10 includes a catheter 14 defining a lumen 16 in which the implant 12 is housed for delivery. Implants 12 of the device generally include a plurality of anchors 20a-20c interconnected with a cinching member 22. Although only three representative anchors 20a-20c are shown, additional anchors can be included. It is further envisioned that each of the anchors 20a-20c can be similarly configured or can be differently configured, as desired. In the example of FIG. 1, the implant 10 is arranged in the catheter 14 in a loaded arrangement in where the anchors 20a-20c are stacked. In various embodiments, the cinching member 22 is a flexible, elongated member such as a suture, wire, filament, cord or the like that is suitable for being surgically implanted. In one example, the cinching member 22 is made of aramid fibers. In some embodiments, the cinching member 22 is a single continuous member interconnecting the plurality of anchors 20a-20c. If all the anchors 20a-20c are connected with a single cinching member, it may be preferable to have that wire initially extend freely through all the intermediate anchors 20a-20c (all anchors but the first and last). Having the cinching member 22 extending freely through the intermediate anchors 20b-20c is believed to provide the physician with the freedom to move each intermediate anchor 20b-20c as much as desired along the annulus before deployment into the annulus. Such a configuration may also help prevent the next anchor in line from being pulled down and out of the catheter 14 (before such action is intended) while the one before it is being rotated and deployed. In another example, the cinching wire 22 can be fixedly secured to each of the plurality of anchors 20a-20c.

In another example, the cinching member 22 may be an assembly comprised of a plurality of discrete segments, one segment fixedly secured to and interconnecting two adjacent anchors 20a-20c. The implant 10 defines a plurality of segments, each segment including two adjacent anchors (e.g., 20a and 20b or 20b and 20c) and the cinching member 22 interconnecting the two adjacent anchors. Embodiments of the disclosure allow for selective length adjustment of the cinching member between the two adjacent anchors, thus correspondingly allowing for selective spacing between the two adjacent anchors.

Figure 3A:
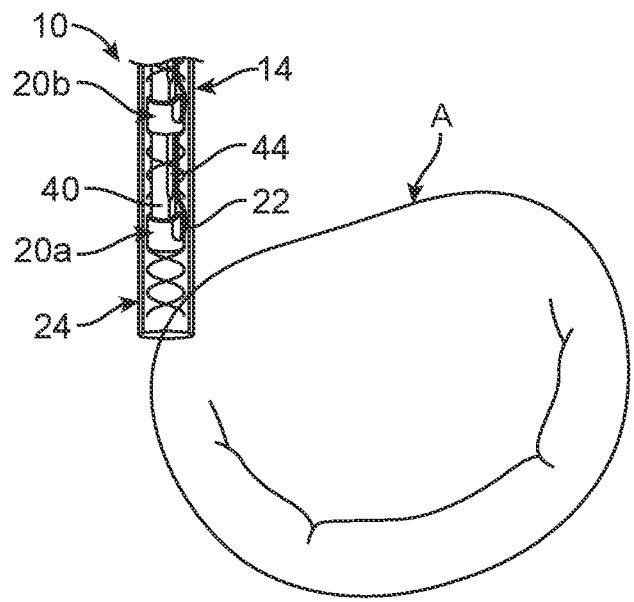
FIGS. 3A-3G illustrate implantation of the implant with the delivery device of FIG. 1 at a heart valve annulus to reshape the valve annulus.
Figure 3B:
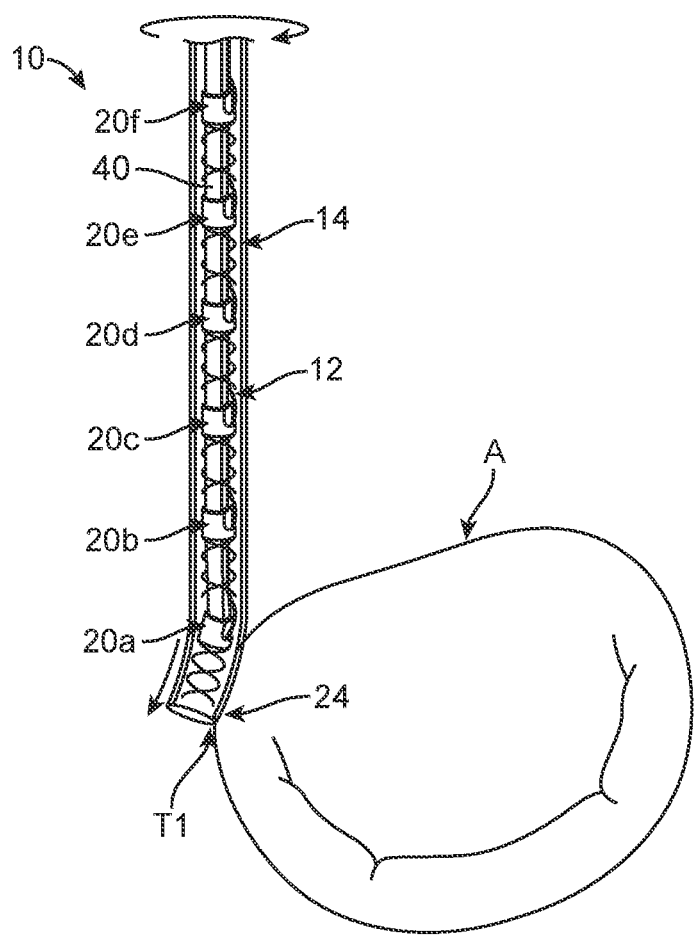

Anchors 20a-20c of the disclosure can take many forms. As indicated above, each anchor 20a-20c of the implant 12 can be identical or can be of a varying configuration. In one example, each anchor 20a-20c includes a head 30 in which the cinching member 22 is received. In one example, the head 30 includes a channel 32 that can optionally be at least partially exposed to receive the cinching member 22. Extending from the head 30 is a prong assembly 34, 34'. The head 30 includes a body 36 defining an opening 38, which can be a recess, for receiving a drive shaft 40 of the system (see also, FIGS. 3A and 3B for example as the drive shaft 40 is omitted in other figures for ease of illustration). In one non-limiting example, the opening 38 can be D-shaped. The drive shaft 40 engages the head 30 and can rotate the respective anchor 20a-20c to drive the anchor into tissue and/or wrap a portion 23 of the cinching member 22 around the anchor 20a-20c to shorten a length of the cinching member 22 between adjacent anchors 20a-20c.

In the examples of FIGS. 1-2, the prong assembly 34, 34' may include a plurality of helically intertwined prongs 42 encircling an optional spike 44. In one example, the distalmost and proximal most anchors do not include a spike (similar to anchor 20a) and each of the intermediate anchors positioned between the distalmost and proximal most anchors do include the spike 44 similar to anchors 20b, 20c. The prong assembly 34, 34' can be made of stainless steel, spring steel, or Nitinol, for example. Optionally, the spike 44 can include a protrusion 46. In some embodiments, the prong assembly 34, 34' may include a single helical prong 42. In some examples, the spike 44 has a length that is longer shorter or equal to a vertical length of the helical prongs 42.

Figure 3C:
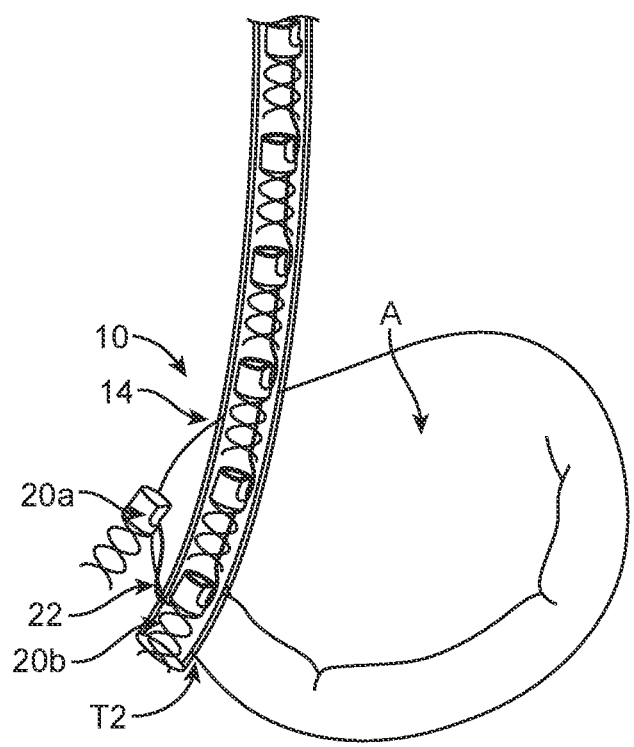

Referring now in addition to FIGS. 3A-3G which illustrate one method of the disclosure. The method includes providing the delivery device 10 in a loaded, delivery arrangement having the implant 12 loaded fully within the lumen 16 such that anchors 20a, 20b, 20c, 20d, 20e, 20f, 20g are stacked within the lumen 16 and the cinching member 22 is serially interconnecting the plurality of anchors 20a-20g. In the loaded arrangement, the drive shaft 40 is inserted through each of the openings 38 in each respective head 30 of each of the plurality of anchors 20a-20g as is perhaps best shown in FIG. 3A. A distal end 24 of the catheter 14 is positioned at a valve annulus A or other bodily lumen to be resized. In one non-limiting example, the valve annulus A is a mitral valve annulus. Once the distal end 24 of the catheter 14 is in the desired starting target site T1, such as a trigone, the implant 12 is distally advanced partially out of the lumen 16 with the drive shaft 40 and a first, distalmost anchor 20a is driven into the annulus A so that the prong assembly 34 is at least partially within the annulus A. This may include engaging the drive shaft 40 with the head 30 of the most proximal anchor 20f and pushing the drive shaft 40 to correspondingly push the most proximal anchor. In another embodiment, the anchors 20a-20g can be configured to be threadably engaged and advanced out of the catheter 14 via rotation of the anchors 20a-20g along the threads (not shown) via engagement and rotation of the drive shaft 40 or other torqueable apparatus. After the distalmost anchor 20a is driven into the annulus A, the drive shaft 40 is proximally withdrawn to disengage the drive shaft 40 from the first anchor 20a. It is noted that the drive shaft 40 is only shown in FIGS. 3A-3B and is omitted from FIGS. 3C-3F for ease of illustration. As shown in FIG. 3C, the distal end 24 of the catheter 14 is moved to a second target site T2 along the annulus A and the second anchor 20b is advanced out of the lumen 16 and partially driven into the annulus A at the second anchor site with the drive shaft 40.

Figure 3D:
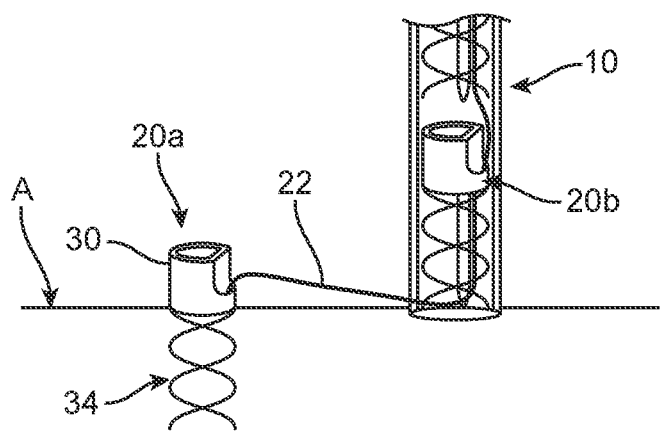
Figure 3E:
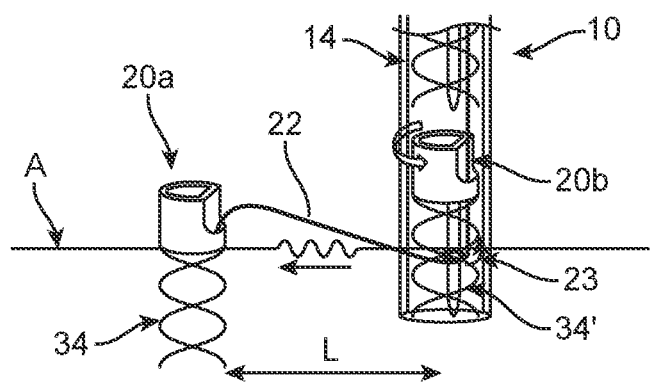
Figure 3F:
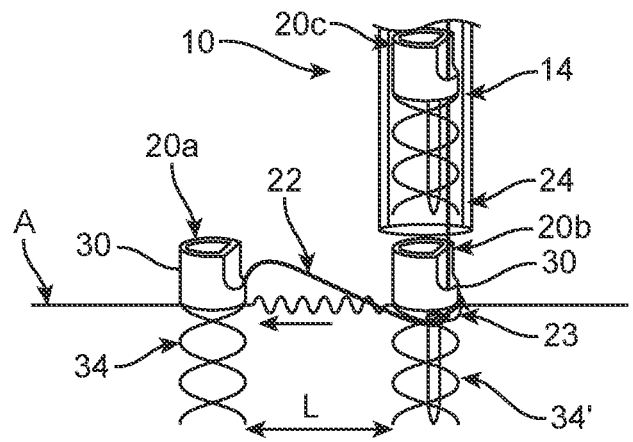
Figure 3G:
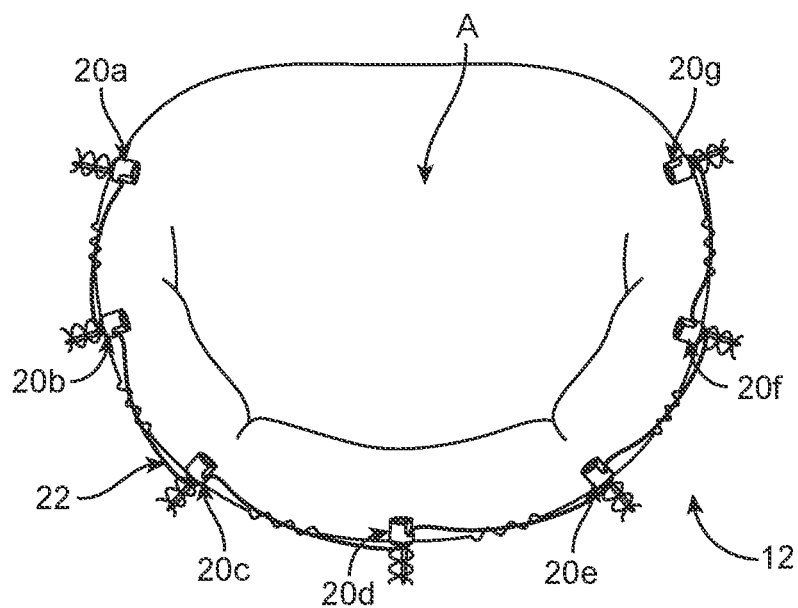

FIGS. 3D-3F are enlarged views of a of twisting-to-cinch sequence between a representative pair of anchors 20a, 20b to reduce a length between the two adjacent anchors 20a, 20b. FIG. 3D shows the cinching member 22 before rotation of the anchor 20b via the drive shaft 40 to wrap the cinching member 22 around the spike 44 of the second anchor 20b. Wrapping of the cinching member 22, shortens a length L of the cinching member 22 between the anchors 20a, 20b which correspondingly pulls the anchors 20a, 20b together to plicate annulus tissue between the first and second anchors 20a, 20b. It is envisioned that the cinching member 22 can be wrapped around the anchor head 30, prongs 34 and/or spike 44 to reduce a length of the cinching member 22 between adjacent anchors 20a, 20b. FIG. 3E illustrates a mid-point of deployment of the second anchor 20b, with cinching member 22 partially wrapped around the spike 44, reducing the length L between the anchors 20a, 20b and causing the valve annulus A tissue to plicate. FIG. 3F image shows the second anchor 20b fully deployed within the valve annulus A tissue and cinching member 22 wrapped around the anchor 20b additional rotations, with the valve annulus A tissue being further plicated and the wrapped cinching member 22 having slid toward a position adjacent the head 30 of anchor 20b. Additional anchors (e.g., anchors 20c-20g) are sequentially deployed in an identical manner around the annulus A and the cinching member 22 is similarly adjusted to plicate tissue between adjacent anchors, as desired. At any stage in the methods of the disclosure, known imaging technologies and techniques may be employed to provide visualization of the implant deployment and adjustment. Once the last, proximal most anchor (e.g., 20g) of the implant 12 is deployed into the annulus A, the catheter 14 and drive shaft 40 can be withdrawn from the final anchor 20g, leaving behind only the implant 12 (comprising the plurality of anchors 20a-20g and the cinching wire 22) in the anatomy as shown in FIG. 3G, for example. In another method, each anchor can be secured to the valve annulus prior to cinching.

The systems and methods of the disclosure are beneficial as there is no need to sever and remove any excess length of the cinch member after cinching or wrapping around the anchor(s). In addition, since the cinching member is fixed to at least the first and last anchors (e.g., 20a, 20g), no locking mechanism to maintain the cinching member is strictly necessary. Also, since the cinching or reshaping of the valve annulus was achieved sequentially through rotation of the anchors, no "final cinch" is required.

Figure 4:
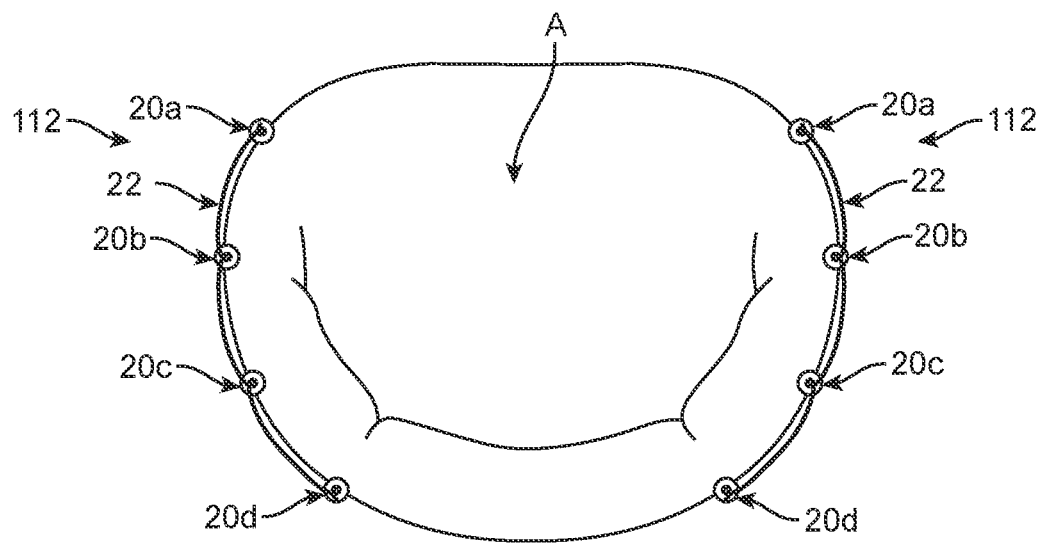
FIG. 4 is a schematic illustration of an alternate arrangement of two implants implanted at the valve annulus to reshape the valve annulus.

In various methods, the implant 12 can be delivered from trigone to trigone, for example as shown in FIG. 3G or two or more implants 112, 112 of the present disclosure be deployed throughout the annulus as shown in FIG. 4. The implants 112 can be any of those disclosed herein, delivered and deployed in any manner disclosed herein. In one example, each implant 112 is identical to implant 12 except that the implant 112 includes a lesser number of anchors (e.g., four anchors).

The number of rotations to "fully" seat one anchor (see, e.g., FIG. 3F) are, in part, dictated by a pitch of the helically-shaped prong(s) 42 (i.e. length per revolution) and an overall length of the prong(s) 42, which may be dictated by an avoidance of damaging or perforating adjacent structures, for example. In one example, an implant for achieving about 60 mm of annular reduction includes 6 anchors, each anchor having a length of 5 mm, a prong diameter of 1.62 mm and at least one helical prong having a pitch of 2.54 mm. In this example, each anchor would be rotated 1.97 revolutions for "full" deployment. In yet another example, an implant for achieving about 10 mm of annular reduction includes 14 anchors, each having a length of 8.5 mm, a prong diameter of 0.035 mm and at least one helical prong having a pitch of 1.27 mm. In this example, each anchor could be rotated 6.69 revolutions for "full" deployment. Based on this data, it is envisioned that, in some embodiments of the disclosure, the cinching member will wrap around the prong or head somewhere in a range between 1.5 and 7 revolutions.

Figure 5:
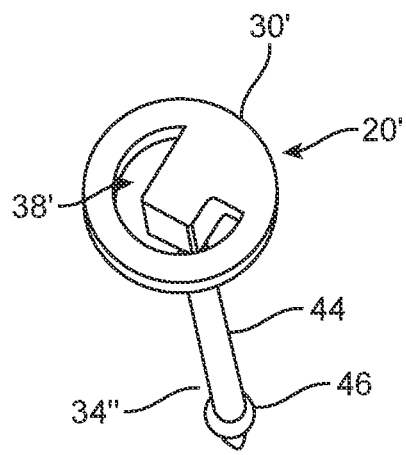
FIG. 5 is a perspective view of an alternate anchor suitable for use with implants of the disclosure.

Any anchor configuration capable of rotational advancement into annulus tissue is envisioned and considered within the scope of the present disclosure. In the example of FIG. 5, an alternate anchor 20' includes a head 30' having an alternate opening 38' configured to be engaged with a correspondingly shaped drive shaft (similar to drive shaft 40) and the anchor 20' includes a prong assembly 34" having only a spike 44 with a protrusion 46.

Figure 6:
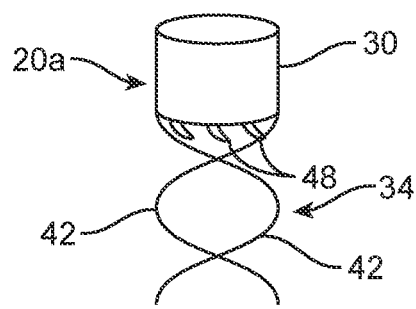
FIG. 6 is a side view of one anchor of FIGS. 1-2 including optional barbs on a head of the anchor.
Figure 7:
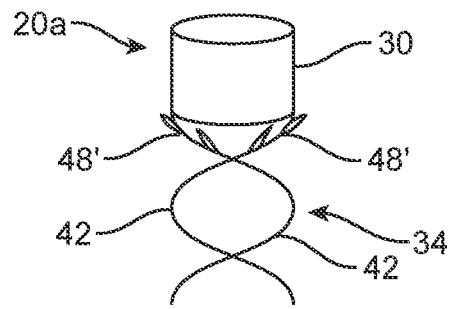
FIG. 7 is a side view of one anchor of FIGS. 1-2 including optional bars positioned on one or more prongs of the anchor.

Referring now in addition to FIG. 6, any anchor of the disclosure can optionally include one or more barbs 48 on the head 30, adjacent the prong assembly 34. In the example of FIG. 6, anchor 20a includes barbs 48 extending from the body 36 of the head 30. In one example, the barbs 48 are angled to restrict disengagement of the prong assembly 34 from the annulus A after the barbs 48 have been inserted into the annulus. In the alternate embodiment of FIG. 7, any anchor of the disclosure can be modified to include barbs 48' positioned on one or more prongs 42. The barbs 48' are angled to restrict disengaging me of the prong assembly 34 from the annulus A.

Figures 8A, 8B:
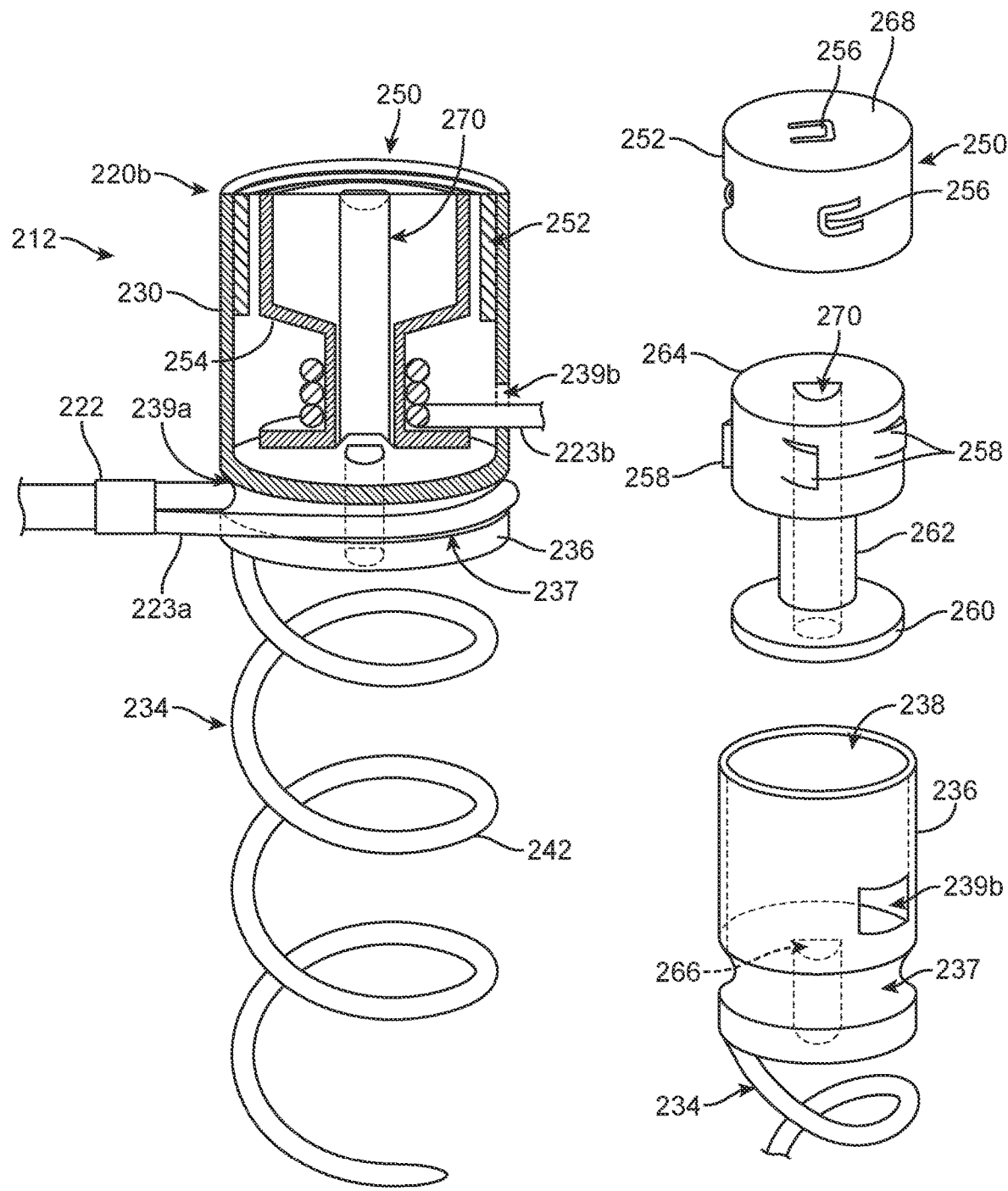
FIG. 8A is a partial, cross-sectional view of an alternate implant including a cinching member interconnecting a plurality of anchors (only one anchor is shown); wherein at least one anchor includes a ratchet assembly.
FIG. 8B is a partial, exploded view of the anchor of FIG. 8A.
Figure 8C:
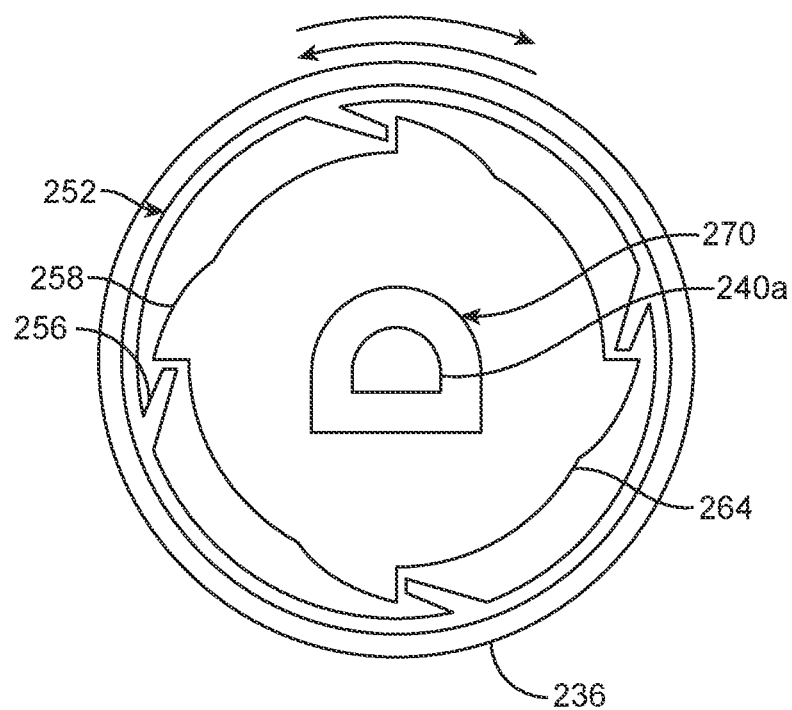
FIG. 8C is a top view of the anchor of FIGS. 8A-8B.

Any implant of the disclosure can include one or more anchors of the disclosure can be configured to include a ratchet assembly to prevent an unraveling of the cinching member during cinching (i.e. wrapping of the cinching member around the anchor). One such delivery device 210 utilizing such anchors 220a, 220b, 220c, 220d is collectively shown in FIGS. 8A-11. With reference to FIGS. 8A-8C, one or more anchors 220b can include a head 230 and a prong assembly 234 extending from the head. In various embodiments of the disclosure, the cinching member 222 includes at least one looped, hold portion 223a, and at least one cinching portion 223b. A body 236 of the head 230 can define a groove 237 in which the hold portion 223a of the cinching member 222 can freely rotate while the anchor 220b is being rotating driven into tissue. In one example, the cinching member 222 includes one hold portion 223a positioned around each anchor (e.g., 220a, 220b, 220c, 220d) of the implant 212 and one cinching portion 223b arranged to wrap around each intermediate anchor spool 254. The prong assembly 234 of each anchor (e.g., 220a-220d) can be any of the types disclosed herein. In the example shown, the prong assembly 234 includes a helical prong 242. An opening 238 in the body 236 of the head 230 houses the ratchet assembly 250. In one example, the ratchet assembly 250 includes a lock tube 252 and a spool 254. The lock tube 252 includes a plurality of cams 256 configured to engage a plurality of teeth 258 of the spool 258. In one example, the cams 256 are formed from cutouts in the lock tube 252. As the spool 254 rotates within the lock tube 252, the plurality of teeth 258 are configured to slide past the cams 256 in one direction (e.g., clockwise) and are configured to be blocked from further movement within slots if the spool 254 rotates in the opposite direction (e.g., counterclockwise). In this way, winding of the cinching member 222 can be maintained around the spool 254. Should a drive shaft 240, which is configured to drive the rotation of the spool 254, be released and tension of the cinch member 222 be at least momentarily lost, the ratchet assembly 250 will substantially maintain the position and tension within the cinch member 222. Although four cams 256 and four teeth 258 are shown, alternate examples of the disclosure include more or fewer cams 256 and teeth 258.

The ratchet assembly 250 can take many configurations. In one example, the spool 254 includes a first portion 260, a second portion 262 and a third portion 264. The second portion 262 interconnects the first portion 260 to the third portion 264 and has a reduced diameter with respect to the first and third portions 260, 264 to maintain the spooled cinching member 222 around the second portion 262 as is generally shown in FIG. 7A. In the example of FIGS. 8A-8C, the cinching member 222 extends from around the groove 237 into a first aperture 239a formed in the body 236 to the second portion 262 of the spool 252 where the cinching member 222 can extend approximately 180 degrees to exit a second opening 239b in the body 236 to extend to the adjacent anchor (e.g., anchor 220c). During anchor placement, rotation of window 239b will actively unwind the cinching member 223b, which is advantageous as to not alter said anchoring position or previous anchor position and integrity.

Figure 9:
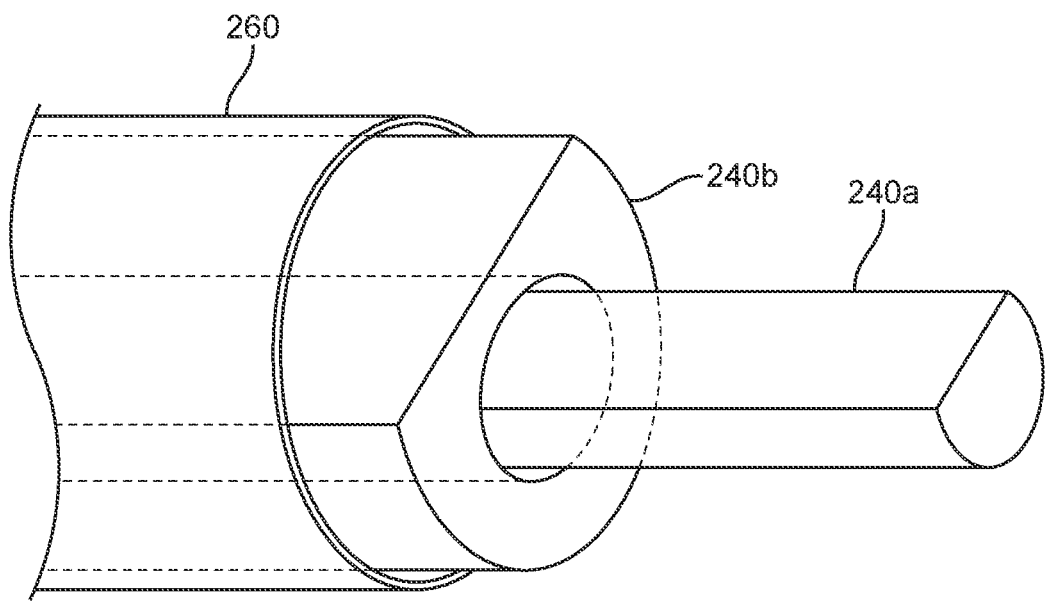
FIG. 9 is a perspective view of drive shafts that can be used to rotate components of the anchor of FIGS. 8A-8C.

Referring now in addition to FIG. 9, the delivery device 210 can be provided with two drive shafts 240a, 240b. The first drive shaft 240a is configured and arranged to extend within an apertures 268, 270 of the lock tube 250 and spool 254 to an aperture 266 within the body 236 of the head 230. The first drive shaft 240a is configured to be able to distally advance (i.e. push the anchor 220b out of the catheter 14) and rotatingly drive the anchor 220b into the annulus or other tissue. The second drive shaft 240b is configured to selectively engage and rotate the spool 254 to wind the cinching member 222 about the second portion 262, reducing a length between two adjacent anchors.

Figure 10:
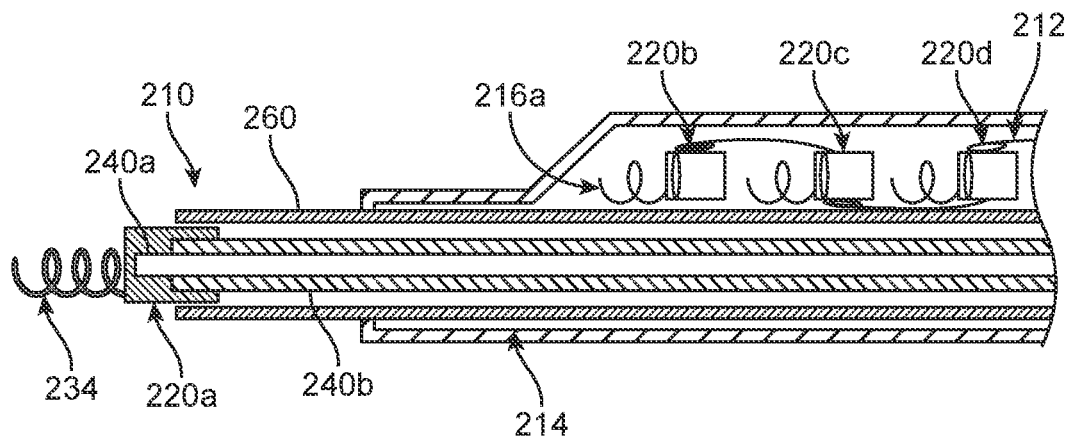
FIG. 10 is a partial, cross-sectional view of a delivery device that can deliver the implant of FIG. 7, the delivery device including the drive shafts of FIG. 9.
Figure 11:
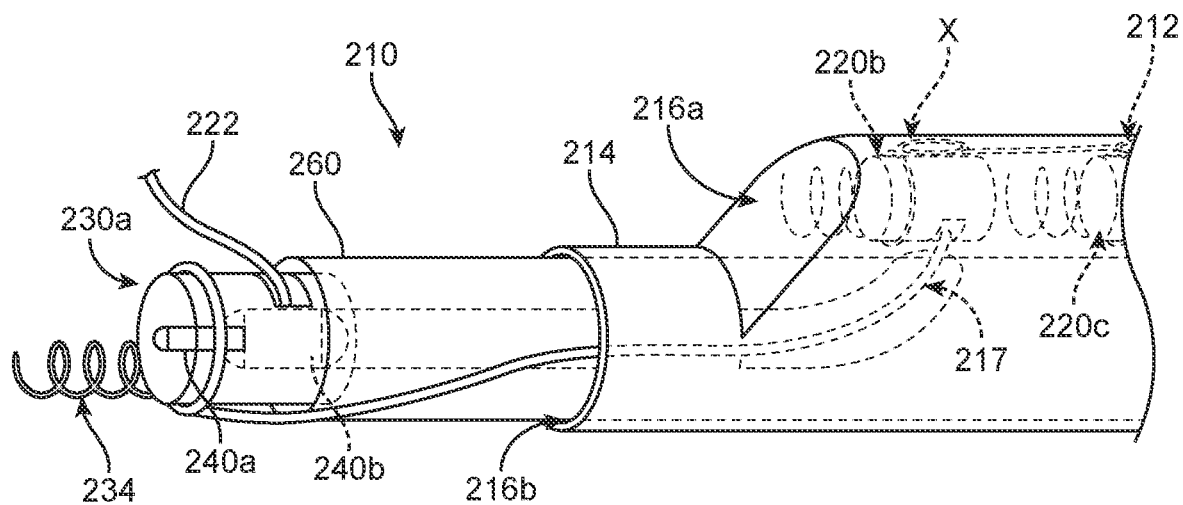
FIG. 11 is a partial, perspective view of the delivery device of FIG. 10.

The delivery device 210 is best shown collectively in FIGS. 9-11. In this example, the delivery device 210 includes a catheter 214 having a first lumen 216a and a second lumen 216b. The first lumen 216a intersects the second lumen 216 at junction 217. The anchors 220a-220c are spring loaded into the first lumen 216a and biased in a distal direction when a drive sheath 260 and drive shafts 240a, 240b are retracted. This is done in such a manner that the next anchor within the first lumen 216a to be deployed enters the second lumen 216b via biasing (i.e. spring) force placed on the anchors within the first lumen 216a and the internal geometries of the first lumen 216a and the second lumen 216b at junction 217. Then, the drive shafts 240a, 240b and the drive sheath 260 are advanced distally to prevent the next anchor in the series from entering the second lumen 216b and keeping the cinching member 222 in the interstitial space between the first lumen 216a and the second lumen 216b. Having the cinching member 222 in this space prevents the cinching member 222 from becoming tangled around the drive shafts 240a, 240b during anchoring of the implant into tissue. In one example, at least a portion of the cinching member 222 is loaded into the first lumen 216b in a serpentine orientation at position X, similar to fire hose stacking, to allow for stack in the cinching member 222 during loading and deployment of the anchors. This delivery system 210 is believed to be most suitable for implants having a fixed or predetermined number of anchors.

Figure 12:
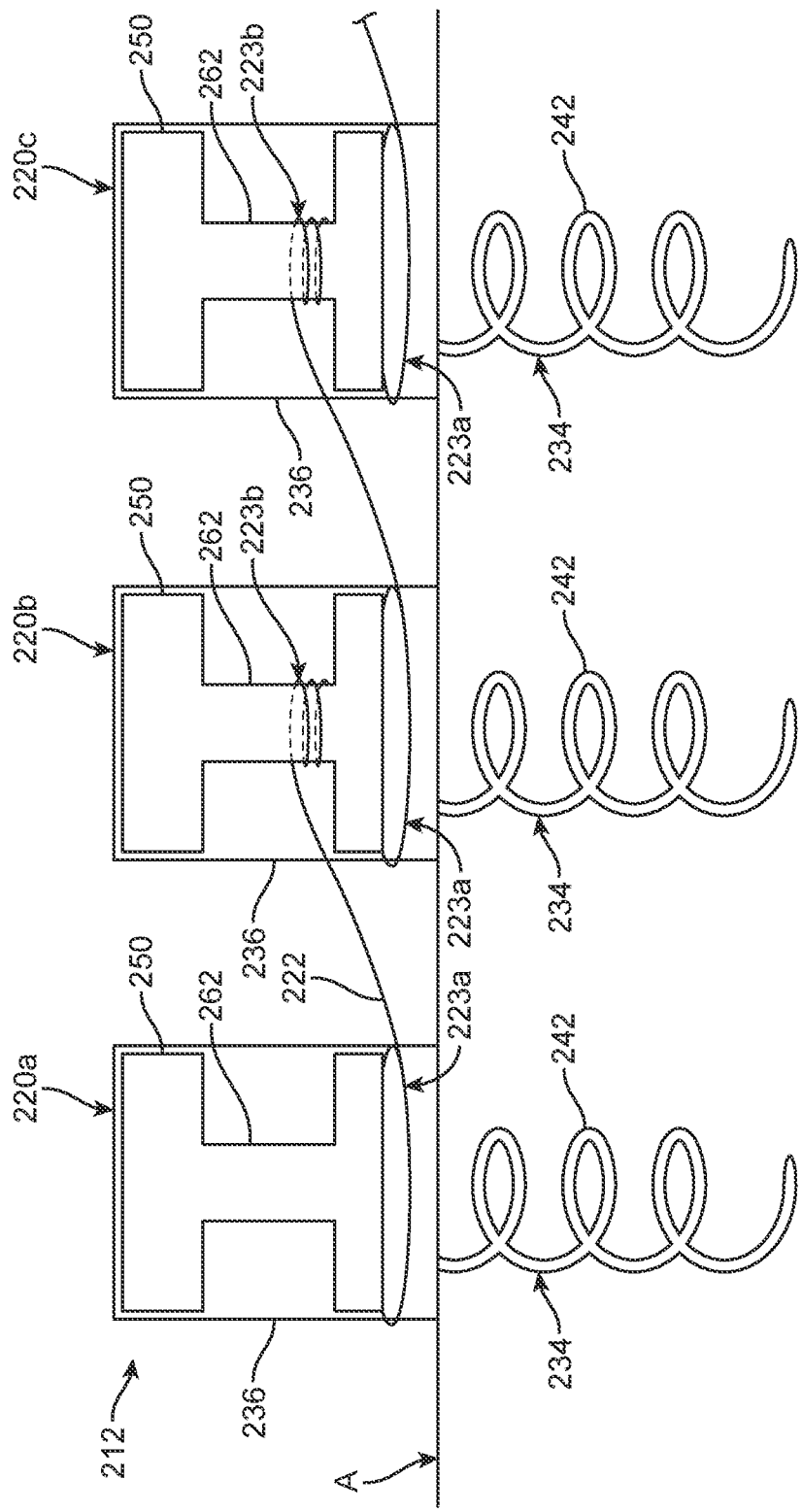
FIG. 12 is a partial, side view of the implant, which has been implanted to size an annulus.

Referring now in addition to FIG. 12, which illustrates a portion of implant 210 that can be delivered with the delivery device 210. The implant 212 can include two or more anchors (anchors 220a, 220b, 220c are shown). As illustrated in FIG. 10, the implant 212 can have at least four anchors 220a, 220b, 220c, 220d. Each anchor 220a, 220b, 220c can be identically or differently configured. In the illustrated example, the proximal most anchor (not shown) and the distalmost anchor 220a can be fixedly secured to the cinching member 222, whereas the cinching member 222 is not fixed to the intermediate anchors (e.g., 220b, 220c). In this example, the distalmost anchor 220a is delivered to and deployed into the tissue or annulus A with the first drive shaft 240a, which pushes the anchor 220a distally and rotates the anchor 220a to drive the prong assembly 234 into the annulus A. Then, the first drive shaft 240a is proximally withdrawn to disengage from the first anchor 240a and the catheter 214 is moved to the next target location and then the second anchor 220b is deployed from the catheter 214 and into the annulus A. The first drive shaft 240a is again used to engage the second anchor 220b, drive the second anchor 220b distally out of the catheter 214. Rotation of the first drive shaft 240a correspondingly rotates the body 236 and the prong assembly 234 to at least partially drive the prong assembly 234 into the annulus A. Should placating of the annulus A between the first and second anchors 220a, 220b be desired, the second drive shaft 240b can be engaged with the spool 254 to rotate the spool 254 and wind the cinching member 254 around the second portion 262 to the degree desired to bring the anchors 220a, 220b closer together, placating the tissue between the anchors 220a, 220b. As the second drive shaft 240b is winding the cinching member 222, the ratchet assembly 250 substantially maintains the degree of spooling as the spool 254 cannot be rotated in the opposite direction an amount greater than the location of the next cam 256. In the example of four equally spaced cams 256, the maximum amount of unwinding possible would be 90 degrees.

Yet another ratcheting implant 312 and delivery device 310 embodiment is schematically illustrated in FIGS. 13A-15C. In this example, the implant 312 includes a plurality of anchors 320a, 320b, 320c serially connected by a cinching member 322, which can be any of the type disclosed herein. Each anchor 320a, 320b, 320c of the implant 312 includes a head 330 having an opening 338 maintaining a ratchet assembly 350 including a ratchet 354 having a plurality of teeth 358 (generally referenced). Extending from an inner surface of the head 330 and into the opening 338 is at least one pawl 356 configured to allow the ratchet 354 to rotate in one direction (e.g., clockwise) but not in the other direction (e.g., counter-clockwise) with respect to the head 330. Each anchor 320a, 320b, 320c can include a prong assembly 334 and can be otherwise configured similar to any other anchor disclosed herein. One method of deploying the implant 312, anchors 320 and adjusting a length of the cinching member 322 between adjacent anchors is schematically depicted in FIGS. 14A-15C. In this example, the delivery device 310 is provided in a loaded state in which the implant 312 is loaded within a lumen 316 of a catheter 314. The distalmost anchor 320a is deployed out of the catheter 314 and into the annulus A or other tissue at a target site. The catheter 314 is moved to a second target site at the annulus A and, as shown in FIG. 14A, then the next anchor 320b is advanced out of the catheter 314 with the drive shaft 340, which can be similarly configured and operate in a manner similar to drive shaft 40 or any other drive shaft disclosed herein. The drive shaft 340 further rotates the anchor 320b to drive the prong assembly 334 of the anchor 320b into the annulus A. Rotation of the anchor 320 further wraps the cinching member 322 around the head 330, to shorten a length of the cinching member 322 between the adjacent anchors (e.g., 320a and 320b or 320b and 320c), placating the annulus/tissue between the anchors in the process (see FIGS. 14B and 14C as well as FIGS. 3E-3F, for example). The outer member is rotated in the opposite direction of the drive shaft to ensure tension on cinching member 322 only drives the anchor 334 further in, ie not unscrewing it. Then, the catheter 314 and drive shaft 340 are detached from the anchor 340 as shown in FIG. 14D. Additional anchors 320c of the implant 312 can be implanted in the same manner. FIGS. 15A-15C, schematically illustrate the implantation of the implant 312 having three anchors 320a, 320b and 320c and how the implant 312 is transitioned in the corresponding stages of FIGS. 14A-14C. It is to be understood that the catheter 314, cinching member 322 and anchor(s) 320a, 320b, 320c can include features disclosed herein with respect to other embodiments having similarly named elements.

The delivery device 310 of FIGS. 14A-14D can be modified as shown in FIGS. 16A-17E to include a sleeve 370 positioned within the lumen 316 of the catheter 314, and between the ratchet 354 and the pawl 356. In this example, preventing unwinding (i.e. uncinching or increasing a distance between adjacent anchors) of the cinching member 322 as it is wrapped around the anchor 320b as is shown in FIG. 17C can be delayed until the sleeve 370 is proximally withdrawn as is shown in FIG. 17D so that the pawl 356 can engage the ratchet teeth 358 (generally referenced; see FIG. 16D). FIGS. 18A-18D, schematically illustrate the implantation of the implant 312 having three anchors 320a, 320b and 320c and how the implant 312 is transitioned in the corresponding stages of FIGS. 17A-17D with the delivery device 310 having the sleeve 370. It is to be understood that the catheter 314, cinching member 322 and anchor(s) 320a, 320b, 320c can include features disclosed herein with respect to other embodiments having similarly named elements.

Referring now in addition to FIGS. 19A-21D, which schematically illustrate yet another delivery device 410 for delivering an implant 412 having a plurality of anchors 420a, 420b, 420c (see FIG. 21A) serially connected with a cinching member 422 of any of type of the present disclosure. In this example, one or more anchors 420a, 420b, 420c includes a head 430 having an opening 438 in which a ratchet assembly 450 is provided. Each anchor 420a, 420b. 420c can include a prong assembly 434 and can be otherwise configured similar to any other anchor disclosed herein. The catheter 414 is moved to a target site at the annulus A and, as shown in FIG. 20A, then the next anchor 420b is advanced out of the catheter 414 with the drive shaft 440, which can be similarly configured and operate in a manner similar to drive shaft 40 or any other drive shaft disclosed herein. The ratchet assembly 450 includes a ratchet 454 having a plurality of ratchet teeth 458 (generally referenced). The ratchet assembly 450 further includes one or more bosses 456 extending radially inward from an inside surface of the head 430. The cams 456 are configured to engage the ratchet teeth 458 and restrict rotation of the ratchet 454 in one rotational direction. To fully lock the rotational position of the ratchet 454 with respect to the head 430, a locking ring 470 can be advanced distally from within a lumen 416 of a catheter 414 of the delivery device 410 to a position between the ratchet 454 and the bosses 456 (FIG. 19D). In one example, the locking ring 470 is advanced by pushing or the like with an inner catheter 472 within lumen 416. The locking ring 470 is arranged and configured to prevent further rotational movement in either direction (i.e. clockwise or counterclockwise) of the ratchet 454. In an alternate embodiment, potting adhesive (which could similarly be referenced by reference numeral 470) could be applied between the ratchet 454 and the bosses 456 with a tool (e.g., 472 or the like) housed within the lumen 416. Although the ratchet 454 is shown to have four ratchet teeth 458 and the head 430 is shown to have four bosses 456, fewer or greater number of these respective elements are within the scope of the present disclosure.

It is envisioned that aspects of the disclosure are suitable for a variety of additional treatment applications. For example, systems, devices and methods of the disclosure are believed to be suitable for atrial appendage closure procedures in which an implant of the disclosure is delivered via transcatheter approach for implantation at an atrial appendage for closing the appendage. In addition, systems, devices and methods of the disclosure are believed to be suitable for gastric restriction or diameter reduction procedures in which the implants of the disclosure are anchored within the gastrointestinal tract for gastric reduction. It is further envisioned that systems, devices and methods of the disclosure may be suitable for the treatment of urinary incontinence in which implants of the disclosure can be deployed at the urethra for urethra restriction. In light of the present disclosure, additional bodily lumen reshaping and reduction procedures, which desire a minimally invasive approach, may be accomplished with the techniques of the disclosure. Therefore, any description or drawing of a bodily lumen that is disclosed herein as an annulus can be interchanged with another bodily lumen or bodily tissue site.

It should be understood that various aspects disclosed herein may be combined in different combinations than the combinations specifically presented in the description and accompanying drawings. It should also be understood that, depending on the example, certain acts or events of any of the processes or methods described herein may be performed in a different sequence, may be added, merged, or left out altogether (e.g., all described acts or events may not be necessary to carry out the techniques). In addition, while certain aspects of this disclosure are described as being performed by a single module or unit for purposes of clarity, it should be understood that the techniques of this disclosure may be performed by a combination of units or modules associated with, for example, a medical device.

What is claimed is:

1. A method of delivering an implant, the method comprising:
    providing a delivery device including a catheter defining a lumen, the delivery device being in a loaded arrangement in which the implant is positioned within the lumen, the implant having a plurality of anchors connected in series by a cinching member, the plurality of anchors including a first anchor, and a second anchor;
    delivering a distal end of the catheter to a first target site and deploying the first anchor into the first target site;
    moving the distal end of the catheter to a second target site and partially deploying the second anchor into the second target site; and
    rotating the second anchor at the second target site to wrap the cinching member around the second anchor to shorten a first distance between the first and second anchors.

2. The method of claim 1, wherein the cinching member is wrapped at least one revolution around the second anchor.

3. The method of claim 1, wherein the second anchor includes a head connected to a prong assembly.

4. The method of claim 3, wherein the cinching member is wrapped around the prong assembly or the head.

5. The method of claim 1, wherein the second anchor includes a ratchet assembly having a cam and a spool around which the cinching member is wrapped, wherein the ratchet assembly restricts rotation of the spool in one direction.

6. The method of claim 5, further comprising a locking sheath positioned between the spool and the cam so that the cam is separated from the spool, the method further comprising withdrawing the locking sheath so that the cam can engage the spool.

7. The method of claim 1, wherein the plurality of anchors includes a third anchor; wherein the method further includes moving the distal end of the catheter to a third target site and at least partially deploying the third anchor into the third target site; the method further including rotating the third anchor at the third target site to wrap the cinching member around the third anchor to shorten a second distance between the second anchor and the third anchor.

8. The method of claim 1, wherein the first target site is at a heart valve annulus.

9. The method of claim 1, wherein the first target site is an atrial appendage.

10. The method of claim 1, wherein the first target site is within a gastrointestinal tract.

11. The method of claim 1, wherein the first target site is at a urethra.

12. The method of claim 5, wherein the ratchet assembly is disposed within an opening of a head of the anchor.

13. A method of delivering an implant, the method comprising:
    delivering a distal end of a catheter of a delivery device in a loaded arrangement to a first target site, the catheter defining a lumen in which the implant is positioned in the loaded arrangement, the implant having a plurality of anchors connected in series by a cinching member;
    deploying a first anchor of the plurality of anchors into the first target site;
    moving the distal end of the catheter to a second target site;
    partially deploying a second anchor of the plurality of anchors into the second target site; and
    rotating the second anchor at the second target site to wrap the cinching member around the second anchor to shorten a first distance between the first and second anchors; and
    after rotating the second anchor to shorten the first distance, moving the distal end of the catheter to a third target site and partially deploying a third anchor of the plurality of anchors.

14. The method of claim 13, wherein the cinching member is wrapped at least one revolution around the second anchor.

15. The method of claim 13, wherein the second anchor includes a head connected to a prong assembly, and wherein the cinching member is wrapped around the prong assembly or the head.

16. The method of claim 13, wherein the second anchor includes a ratchet assembly having a cam and a spool around which the cinching member is wrapped, wherein the ratchet assembly restricts rotation of the spool in one direction.

17. The method of claim 16, wherein the ratchet assembly is disposed within an opening of a head of the anchor.

18. The method of claim 16, further comprising a locking sheath positioned between the spool and the cam so that the cam is separated from the spool, the method further comprising withdrawing the locking sheath so that the cam can engage the spool.

19. The method of claim 13, further comprising rotating the third anchor at the third target site to wrap the cinching member around the third anchor to shorten a second distance between the second anchor and the third anchor.

20. The method of claim 13, wherein the first target site is at a heart valve annulus.

* * * * *